US011766002B2

(12) United States Patent
Buet et al.

(10) Patent No.: US 11,766,002 B2
(45) Date of Patent: Sep. 26, 2023

(54) METHOD FOR PRODUCTION OF STERILE FLOWERING BIOMASS IN TEMPORARY IMMERSION BIOREACTORS

(71) Applicant: ALKION BIOINNOVATIONS, Boulogne-Billancourt (FR)

(72) Inventors: Sarah-Meryll Buet, Boulogne-Billancourt (FR); Elisa Fiume, L'etang la Ville (FR); Gabriel Guihard, Les Essarts-le-Roi (FR); Leo-Paul Tisserant, Saint-Cyr-L'ecole (FR)

(73) Assignee: ALKION BIOINNOVATIONS, Boulogne-Billancourt (FR)

( * ) Notice: Subject to any disclaimer, the term of this patent is extended or adjusted under 35 U.S.C. 154(b) by 0 days.

(21) Appl. No.: 17/765,385

(22) PCT Filed: Sep. 30, 2020

(86) PCT No.: PCT/EP2020/077317
§ 371 (c)(1),
(2) Date: Mar. 30, 2022

(87) PCT Pub. No.: WO2021/063996
PCT Pub. Date: Apr. 8, 2021

(65) Prior Publication Data
US 2022/0330496 A1 Oct. 20, 2022

(30) Foreign Application Priority Data
Sep. 30, 2019 (EP) ..................................... 19306219

(51) Int. Cl.
*A01G 22/60* (2018.01)
*A01G 7/06* (2006.01)

(52) U.S. Cl.
CPC .............. *A01G 22/60* (2018.02); *A01G 7/06* (2013.01)

(58) Field of Classification Search
CPC .......... A01H 4/00; A01H 4/005; A01H 4/008; A01H 1/1215; A01H 4/001; A01H 4/002; A01H 5/02; A01H 5/12; A01H 6/28; A01B 39/12; A01G 2/00; A01G 22/60; A01G 22/15; A61K 2039/517; A23V 2250/21; C12N 5/0025; C12N 5/04; C12N 5/0671; C12N 5/0677; C12N 5/14; C12N 2500/00; C12Q 2600/13; A61L 27/3895; Y10S 977/923; Y10S 435/809
See application file for complete search history.

(56) References Cited

U.S. PATENT DOCUMENTS

2009/0055968 A1 * 2/2009 Rudrabhatla ............ C12N 5/04
800/278

FOREIGN PATENT DOCUMENTS

| WO | WO-96/25484 A1 | 8/1996 | |
| WO | WO-2011/030083 A1 | 3/2011 | |
| WO | WO-2011030083 A1 * | 3/2011 | ............... A01H 4/00 |
| WO | WO-2012/146872 A1 | 11/2012 | |
| WO | WO-2016/092098 A1 | 6/2016 | |
| WO | WO-2019/006466 A1 | 1/2019 | |
| WO | WO-2019/006470 A1 | 1/2019 | |

OTHER PUBLICATIONS

Murthy et al ("In vitro flowering—A review", Journal of Agricultural Technology, 2012, vol. 8(5): 1517-1536) (Year: 2012).*
Georgiev et al, "Temporary immersion systems in plant biotechnology", Engineering in Life Sciences, 2014, 14, 607-621 (Year: 2014).*
Sayed Hussein, dissertation "Cannabinoids production in *Cannabis sativa* L.: An in vitro approach", 2014 pp. 82-88 (Year: 2014).*
Elie Dolgin, A boosted crop, The bioengineering of cannabis, Nature 572, S5-S7, Aug. 28, 2019, downloaded from nature.com/articles/d41586-019-02525-4 (Year: 2019).*
Alvard et al., "Comparison of methods of liquid medium culture for banana micropropagation" Effects of temporary immersion of explants, Plant cell, Tissue and Organ Culture, vol. 32: p. 55-60, (1993).
Neil R. Baker, "Chlorophyll Fluorescence A Probe of Photosynthesis In Vivo" Annual Review of Plant of Biology, vol. 59, pp. 89-113, (2008).
Berman et al., "A new ESI-LC/MS approach for comprehensive metabolic profiling of phytocannabinoids in Cannabis" Scientific Reports, vol. 8, pp. 1-15, Sep. 2018.
Chandra S, et al, Cannabis cultivation: Methodological issues for obtaining medical-grade product, Epilepsy Behavior, pp. 1-11, (2016).

(Continued)

*Primary Examiner* — Susan McCormick Ewoldt
(74) *Attorney, Agent, or Firm* — MARSHALL, GERSTEIN & BORUN LLP (57) ABSTRACT

The present invention relates to a method for producing sterile flowering biomass, the method comprising: a) inoculating a temporary liquid immersion culture system containing a sterile culture medium containing at least one cytokinin with sterile plant material, b) growing leafy biomass, and c) inducing and maturing flower tissues from the leafy biomass, wherein flowering is induced by reducing the duration and/or frequency of the immersion of the plant material in the culture medium in step c) compared to step b). It further relates to a method for producing a component present in flowering biomass, using sterile flowering biomass obtained using the aforementioned method according to the invention.

19 Claims, 3 Drawing Sheets

(56) References Cited

OTHER PUBLICATIONS

Driver et al., "In vitro propagation of Paradox Walnut root stock" HortScience, American Society for Horticultural Science, vol. 19(4): pp. 507-509, Aug. 1984.

Florez et al "A Temporary Immersion Plant Propagation Bioreactor with Decoupled Gas and Liquid Flows for Enhanced Control of Gas Phase" American Institute of Chemical Engineers, Biotechnology. Prog., vol. 32, No. 2, (2016).

Georgiev et al., "Temporary immersion systems in plant biotechnology" Engineering in Life Sciences, vol. 14, pp. 607-621, (2014).

Lata et al., "High Frequency Plant Regeneration from Leaf Derived Callus of High Δ9-Tetrahodrocannabinol Yielding *Cannabis sativa* L." Planta Med, vol. 76, pp. 1629-1633, (2010).

Lata, H. et al., "In vitro mass propagation of *Cannabis sativa* L.: A protocol refinement using novel aromatic cytokine meta-topolin and the assessment of eco-physiological, biochemical and genetic fidelity of micropropagated plants" J. Appl. Res. Med. Aromat. Plants, pp. 1-9, (2016).

David J. Potter., "A review of the cultivation and processing of Cannabis (*Cannabis sativa* L.) for production of prescription medicines in the UK" Drug Test. Analysis, vol. 6, pp. 31-38, (2014).

J. Romocea et al., "In Vivo" Propagation of *Cannabis sative* L. Var. Ermo Annals of the Oradea University, International Scientific Conference, Oradea (2010).

Watt et al., "A Micropropagation System for Cloning of Hemp (*Cannabis sativa* L.) by Shoot Tip Culture" Pak. J. Bot., vol. 41, No. 2: pp. 603-608, (2009).

M. Paula Watt., "The status of temporary immersion system (TIS) technology for plant micropropagation" African Journal of Biotechnology, vol. 11. No. 76, pp. 14025-14035, Sep. 20, 2012.

Etienne et al., "Temporary immersion system in piant micropropagation" Plant Cell, Tissue and Organ Culture, vol. 69, pp. 215-231, (2002).

Sri Rama Murthy et al., "In vitro flowering—A review" Journal of Agricultural Technology, vol. 8, No. 5, pp. 1517-1536, (2012).

Lata et al., "Thidiazuron-induced high-frequency direct shoot organogenesis of *Cannabis sativa* L." In Vitro Cell, Dev. Biological.-Plant, vol. 45, pp. 12-19, (2009).

International Search Report and Written Opinion for Corresponding International Application No. PCT/EP2020/077317, dated Oct. 21, 2020.

\* cited by examiner

METHOD FOR PRODUCTION OF STERILE FLOWERING BIOMASS IN TEMPORARY IMMERSION BIOREACTORS

CROSS-REFERENCE TO RELATED APPLICATIONS

This application is U.S. National Stage of International Patent Application No. PCT/EP2020/077317 filed Sep. 30, 2020, which claims the benefit of priority of European Patent Application No. 19306219.7 filed Sep. 30, 2019, the respective disclosures of which are each incorporated herein by reference in their entireties.

TECHNICAL FIELD OF THE INVENTION

The present invention is in the field of in vitro production of flowers or components mainly accumulating in flowers. It relates to a method for producing sterile flowering biomass, the method comprising: a) inoculating a temporary liquid immersion culture system containing a sterile liquid culture medium containing at least one cytokinin with sterile plant material, b) growing leafy biomass, and c) inducing and maturing flower tissues from the leafy biomass, wherein flowering is induced by reducing the duration and/or frequency of the immersion of the plant material in the culture medium in step c) compared to step b). It further relates to a method for producing a component present in flowering biomass, using sterile flowering biomass obtained using the aforementioned method according to the invention.

BACKGROUND ART

Many chemical compounds of interest have initially been isolated from plants, and are still obtained from plants. However, for some compounds sourcing is unreliable in terms of quantity or quality.

The *Cannabis* market represents a good example and has received a lot of attention lately. Most of current production relies on growing plants indoor or in fields and harvesting the cannabinoid-rich female flowers (Potter, 2014).

Several important flower products have been facing limitations on other levels. Saffron, for example, is a commercially important flower harvested to produce the saffron spice. However, its production is seasonal and has a high labor cost.

A major drawback of current cannabinoids production systems is the lack of control on quality and stability of the product, which are highly dependent on season, climate and plant cycle (Chandra et al., 2017). Moreover, the final product can contain adulterants such as pesticides or heavy metals, leading to health issues for patients.

To circumvent these issues, several groups have tried to develop cell suspension or other in vitro culture tools as alternative production methods. However, cell cultures such as *Cannabis* and Saffron cannot produce their compounds of interest at commercially relevant levels so far. Hence, new methods for in vitro flower production are needed.

The use of temporary immersion bioreactors (TIB) in plant biotechnology is known (Georgiev et al., 2014; Watt 2012). TIB are self-contained sterile environments, in which the plant material is temporary immersed in liquid culture medium.

It has been mostly used for micropropagation of various plants, for example on sugarcane, vanilla, pineapple, strawberry, eucalyptus, pistachio or *cannabis* (Lata et al., 2009, 2010n 2016; Romocea and Grassi, 2010; Wang et al., 2009).

WO2011030083 relates to the induction of leafy biomass from undifferentiated cells. The resulting biomass is cultivated in TIB. WO2016092098 relates to a cost-effective TIB for the growth of plant biomass. WO2019006466 and WO2019006470 relate to the in vitro multiplication of plants or plant parts in TIB, in particular for micropropagation of *Cannabis* plant parts.

However, in all disclosed uses of TIB for plant propagation, only leafy biomass is produced, no flowering being disclosed in TIB, even for flowering plants. For compounds that mainly accumulate in flowers, such as cannabinoids, safranal and picrocrocins, TIB culture has not been seen as an appropriate method of production at commercially relevant levels.

In addition, Sri et al ("In vitro flowering—A review", Journal of Agricultural Technology, 1 Oct. 2012 (2012-10-01), pages 1517-1536) is a review describing the state of the art in the factors influencing the in vitro flowering of many plant species, but not specific teaching concerning *cannabis* is presented. The authors clearly indicate that the media composition or the physical conditions need to be changed in order to induce in vitro flowering. The plant, callus, or even somatic embryos are grown, and then, by changing the media (basal medium, sugar content, hormone ratios), or light in vitro flowering is induced. However, changes to the medium can be problematic in an industrial set up, especially when dealing with sterile plant material. Modifications to the culture medium mentioned in this review would increase the risk of contaminations and therefore of loss of materials. Changing light regimes could also be problematic in large scale production facilities. Moreover, all cited references refer to experiments only done in lab scale, which are not applicable for large scale industrial production.

There is thus a need for methods for in vitro flowering that would permit industrial scale-up and limit contamination risks.

SUMMARY OF THE INVENTION

So far, the methods describing the in vitro production of flowers in other culture systems than TIB had focused on hormone balance, medium composition, light or temperature. However, changes to culture media involve contamination risks not compatible with scale up to industrial levels, and change of light regimes could also be problematic in large scale production facilities. Concerning indoor *cannabis* growing, flowering is generally induced by short photoperiod (Chandra et al., 2017; Potter, 2014).

In the context of the present invention, the inventors surprisingly found that flowering of leafy biomass produced in TIB may be induced by reducing the duration and/or frequency of the immersion of the cultivated plan material after growing of the leafy biomass (see Example 1). This is highly advantageous since the change in duration and/or frequency of the immersion in TIB does not involve contamination risk and is easily scalable. Based on the combination of a specific type of bioreactors (TIB) and a unique immersion switch (only possible with this type of bioreactor), a constant and reliable production of biomass followed by in vitro flowering with highly reproducible yields of metabolites (cannabinoids in this case) is achieved. This technology is scalable for industrial applications.

In particular, for 5 distinct *Cannabis sativa* cultivars for which leafy biomass was grown by immersing the plant material in culture medium containing thidiazuron (TDZ) or Meta-Topolin (mT) during 3 minutes every 6 hours, reducing the immersion duration to 2 minutes every 6 hours induced flowering of the *cannabis* plants in the TIB, and permitted to obtain a cannabinoid content (% of dry weight) much higher than what would be obtained from leafy biomass only. In particular, testing only 2 distinct cytokinins, and without optimizing other parameters, a significant number of flowers were obtained, with all 5 (4 female and 1 male) tested *Cannabis sativa* cultivars. In 2 cases, one of the cultivars showed flowers with one of the two tested cytokinins. Flowering with the other tested cytokinin in those two cases is expected to occur within the weeks after the chosen observation time.

This suggests that the cytokinin can influence flowering time for some cultivars. Moreover, while the total content may somewhat vary depending on the precise *Cannabis sativa* cultivars and the specific cytokinin used in culture medium, a content of at least about 1% of dry weight has been obtained for 4 out of the 5 tested cultivars, and a content of at least about 1.5 of dry weight has been obtained for 3 out of the 5 tested cultivars (see Example 1).

Preliminary results suggest that photoperiod is not a crucial parameter for flower induction in TIB-grown biomass (see Example 2), however, further studies should be performed to evaluate the influence of photoperiod when reducing the duration and/or frequency of the immersion of the cultivated plant material after leafy biomass growth.

In a first aspect, the present invention thus relates to a method for producing sterile flowering biomass, the method comprising the following steps:
 a) inoculating a temporary liquid immersion culture system containing a sterile liquid culture medium containing at least one cytokinin with sterile plant material,
 b) growing leafy biomass, and
 c) inducing and maturing flower tissues from the leafy biomass, wherein flowering is induced by reducing the duration and/or frequency of the immersion of the plant material in the culture medium in step c) compared to step b).

In said method, said temporary liquid immersion culture system is preferably a temporary immersion bioreactors (TIB). Moreover, said cytokinin is preferably a natural or artificial cytokinin belonging to the adenine-type or the phenylurea-type, said culture medium preferably containing from 0.01 to 100 µM, preferably from 0.1 to 10 µM of said cytokinin. Said culture medium may further comprise another plant hormone, preferably an auxin.

In said method, the duration and frequency of immersion of the plant material in the culture medium in steps b) and c) preferably varies from 30 seconds to 15 minutes every 30 minutes to 12 hours, and is preferably reduced by 15 to 70% compared to step b).

Light conditions (photoperiod, type of light and intensity) may also be changed between steps b) and c).

Said method is particularly useful for producing sterile flowering biomass of *Cannabis sativa* cultivars.

The present invention also relates to a method for producing a component present in flowering biomass, the method comprising:
 a) producing sterile flowering biomass from sterile plant material using the method according to the invention, and
 b) collecting or extracting the component from the obtained sterile flowering biomass.

Said method may further comprise:
 c) purifying the collected or extracted component, and
 d) optionally, adding an acceptable carrier diluent, excipient or carrier to the purified component.

Said method is also particularly intended for producing at least one cannabinoid compound (preferably, but not limited to one or more of tetrahydrocannabinol (THC), tetrahydrocannabinolic acid (THCA), cannabigerol (CBG), cannabigerolic acid (CBGA), cannabidiol (CBD), cannabidiolic acid (CBDA), cannabichromene (CBC), and cannabichromenolic acid (CBCA)) from *Cannabis sativa* cultivars.

DESCRIPTION OF THE FIGURES

FIG. 2. Quantification of main cannabinoids in flowering material from 5 different *Cannabis* strains grown in temporary immersion bioreactors. Flowers: all trichome-rich inflorescence tissues, including calyx and sugar leaves. Rest: remaining biomass after collection of trichome-rich parts, composing most of the inflorescence. Main Cannabinoids selected are CBDA, THCA, CBCA and their decarboxylated forms, CBD, THC, and CBC. *: Very small male flowers developed, thus separate quantification was not possible. Moreover, as trichome density was not higher, cannabinoid content is not expected to rise.

DETAILED DESCRIPTION OF THE INVENTION

Method for Producing Sterile Flowering Biomass.

In a first aspect, the present invention relates to a method for producing sterile flowering biomass, the method comprising:
 a) inoculating a temporary liquid immersion culture system containing a sterile culture medium containing at least one cytokinin with sterile plant material,
 b) growing leafy biomass, and
 c) inducing and maturing flower tissues from the leafy biomass, wherein flowering is induced by reducing the duration and/or frequency of the immersion of the plant material in the culture medium in step c) compared to step b).

Step a) (Inoculating a Temporary Liquid Immersion Culture System Containing a Sterile Culture Medium Containing at Least One Cytokinin with Sterile Plant Material)
Plants The method for producing sterile flowering biomass according to the invention has been validated on five different *cannabis* cultivars in parallel experiments and is applicable to any plant that may be cultivated in a temporary liquid immersion culture system. The method may be implemented for monocotyledon or a dicotyledon plants.

In view of their economic interest, the method is particularly intended for producing cannabinoids, or safranal and picrocrocin.

For the production of cannabinoids, plants from the family of Cannabaceae will preferably be used, more preferably from *Cannabis* genera, in particular from *Cannabis sativa*, *Cannabis indica*, *Cannabis rudealis*, and crossings cultivars thereof, most preferably from *Cannabis sativa* cultivars. Among hybrids of *Cannabis sativa*, *Cannabis*

*indica* or both, cultivars known under the names Caramel, Purple Haze, Amazing Haze, Blue Amnesia, and Cannatonic may notably be used. However, since the method has been validated on these 5 distinct cultivars, it is clearly applicable to any *Cannabis sativa* and *Cannabis indica* cultivars.

For the production of safranal and picrocrocin, plants from the family of Iridaceae will preferably be used, more preferably from *Crocus* genera, in particular from *Crocus sativus* cultivars.

Nevertheless, the method may also be used for any plant in which the main interest is the flower or compounds produced in the flower. Among dicotyledon plants, these notably include any of *Cannabis*, Hops, Poppy, Rose, Jasmin, *Hydrangea*, Yarrow, Carnation, *Epiphyllum, Gypsophila*, Blazing star, *Gerbera, Arnica*, and Chrysanthemums, preferably *Cannabis*, Hops, Poppy, Yarrow, and *Arnica*. Among monocotyledon plants, these notably include any of Lys, Iris, Lily, Saffron, Orchid, Tulip, *Anthurium, Lisianthus, Nerine, Gladiolus*, preferably Saffron. The method according to the invention may thus preferably be used for *Cannabis* (in particular plants from *Cannabis* genera, in particular from *Cannabis sativa, Cannabis indica, Cannabis rudealis*, and crossings cultivars thereof, most preferably from *Cannabis sativa* cultivars), Saffron (in particular plants from *Crocus* genera, in particular from *Crocus sativus* cultivars), Hops, Poppy, Yarrow, and *Arnica*, with a particular preference for *Cannabis* (in particular plants from *Cannabis* genera, in particular from *Cannabis sativa, Cannabis indica, Cannabis rudealis*, and crossings cultivars thereof, most preferably from *Cannabis sativa* cultivars).

Plant Parts and Sterilization

The plant material inoculated in a temporary liquid immersion culture system in step a) is some plant material that may be obtained in one of the following manners:

Directly from various plant parts, including cells, stems, leaves, apical meristems, nodal segments, trichomes, inflorescence organs (such as sepals, calyx, stigmas and sugar leaves), or roots. Such directly obtained plant parts are referred to as explants.

Among such explants, those from nodal segments are particularly preferred.

Through differentiation of calli, using plant hormones, preferably cytokinins (see below in section relating to culture medium of step a)); or Through de-differentiation or re-differentiation, growth and amplification of former explants.

Preferably, in particular for plants from the *Cannabis sativa* cultivars, nodal segments from surface-sterilized seeds germinated in vitro will be used for inoculating temporary liquid immersion culture systems in step a).

In order to produce sterile flowering biomass, the explant inoculated into the temporary liquid immersion culture system in step a) should preferably have been sterilized before inoculation when directly obtained from a non-sterile plant part.

Sterilization may be performed by any appropriate method known to those skilled in the art, including washing with ethanol and bleach (a solution with 70-96% ethanol and a solution of bleach containing 0.1 to 10% active chlorine may notably be used), other methods, known by the man of the art, include the use of HgCl, Cl2, Ozone, detergents and surfactants, fungicides and bactericides, or acids.

Alternatively, the explant may be inoculated directly into the temporary liquid immersion culture system in step a) when it has been obtained from plant material already cultured in sterile conditions.

Temporary Liquid Immersion Culture System

The temporary liquid immersion culture system used in the method for producing sterile flowering biomass according to the invention is preferably a temporary immersion bioreactor (TIB).

TIB are self-contained sterile environments, in which the plant material is temporary immersed in liquid culture medium. Many TIB are available to those skilled in the art, as disclosed for instance in Etienne and Berthouly, 2002 and Watt, 2012 (see notably Table 1 and references disclosed therein). Non-limiting examples of temporary immersion bioreactors include tilting and rocking vessels, twin flask systems (such as the BIT® system), or single containers with at least two compartments (such as Recipient for Automated Temporary Immersion (RITA®, WO96/25484), MATIS® (WO2012146872A1), or modified Nagene® polysulfone filtration system of NalgeNunc international), the Bioreactor of Immersion by Bubbles (BIB®). Other TIBs are for instance disclosed in WO2016092098, WO2019006466 and WO2019006470, which are herein incorporated by reference in their entirety.

Preferred TIB for use in the invention include:

the Recipient for Automated Temporary Immersion (RITA®), a TIB in which the upper container containing the plant is linked to the lower compartment containing the medium and internal pressure regulates the movement of medium up or down in such a way that the immersion of cultures can be timed (Alvard et al., 1993, WO96/25484). RITA® TIB are commercially available, for instance from VITROPIC, ZAE Des Avants, 34270 Saint-Mathieu-de-Tréviers, FRANCE).

The MATIS®, a TIB using a technology comparable to RITA®, designed for higher culture volumes (WO2012146872A1). MATIS® TIB are commercially available, for instance from CID Plastiques, 50 rue de l'Oliveraie, ZAC Les Jasses, 34130 VALERGUES, France.

The type of TIB disclosed in WO2016092098, which is based on the principle of a porous solid substrate upon which the cells reside that is immersed in liquid growth medium for short periods of time, and comprises (see in particular FIGS. 1-8, and their description):

a growth chamber having one or more transparent side walls and a mesh bottom, to receive plant material;

a flexible bag formed from a transparent material; the flexible bag having dimensioned to receive the growth chamber together with a liquid medium;

an outer chamber having one or more transparent side walls, the outer chamber being formed to receive the growth chamber within the flexible bag.

a driving mechanism arranged to selectively drive movement of the growth chamber along a single axis, allowing the immersion of the mesh bottom and the plant material during operation. Various driving mechanisms may be used, as disclosed in FIGS. 3 and 7-8 of WO2016092098.

No matter which driving mechanism is used, it preferably includes a timer to control operation of the driving mechanism and thereby, in use, control movement of the growth chamber between the first and second positions, thereby controlling the duration and frequency of immersion.

No matter which type of TIB is used in the method for producing sterile flowering biomass according to the invention, the volume of culture medium in said TIB is preferably from 1 to 10 000 L, preferably from 1 to 5 000 L, from 1 to 1 000 L, from 1 to 500 L, more preferably from 1 to 300 L, from 1 to 100 L, from 1 to 50 L, or from 1 to 10 L, depending on the desired scale-up for the production.

Sterile Liquid Culture Medium

The temporary liquid immersion culture system in which the sterile plant material is inoculated in step a) contains a sterile liquid culture medium containing at least one cytokinin.

The sterile liquid culture medium is based on a sterile basal culture medium containing all nutrients necessary for growth, including:
- a solution of salts supplying the macro and micro-elements necessary for the growth of whole plants,
- a carbon source (usually sucrose); and
- optionally, various vitamins, various amino acids and/or various undefined supplements (such as extracts from yeast, meat, malt, various fruits and plants, protein hydrolysates).

Any suitable basal culture medium suitable for plant propagation in vitro may be used, such as the following commercially available media: MS (Murashige and Skoog) medium, DKW medium (Driver and Kuniyaki Walnut medium, Driver J A, Kuniyuki A H, 1984, In vitro propagation of Paradox walnut rootstock. Hortscience 19: 507-509), B5 (Gamborg) medium, WPM (Woody Plant Medium) medium, or SH (Schenk and Hildebrandt) medium, preferably MS, DKW, SH or B5 medium, more preferably MS or DKW medium. All of these media are commercially available, for instance from Sigma Aldrich.

The concentration at which the basal culture medium is used is typically 2×, 1× or 0.5×.

Addition of macroelements (N, P, K) can be considered to further optimize growth and metabolism.

The carbon source can be selected from sugars such as glucose, fructose or more commonly sucrose. Sugar concentration in the culture medium is preferably in the range from 10 to 60 g/l (corresponding to 1 to 6% sugar, preferably sucrose), preferably from 15 to 40 g/L (i.e. 1.5 to 4%), from 20 to 40 g/L (i.e. 2 to 4%), from 25 to 35 g/L (i.e. 2.5 to 3.5%), usually around 30 g/L (i.e. 3%). High sugar concentration in the culture medium may cause osmotic stress, having potential detrimental effect on growth but potentially inducing cannabinoids biosynthesis. In contrast, low sugar concentration in the culture medium may also limit growth due to insufficient energy available to the plants.

Vitamins are preferably present in the liquid culture medium, and may be selected from the following commercially available vitamins: MS vitamins, DKW vitamins, B5 vitamins, WPM vitamins, SH vitamins, preferably used in conjunction with the corresponding basal culture medium. Addition or suppression of vitamins and microelements can be considered to further optimize growth and metabolism.

The sterile liquid culture medium also contains at least one cytokinin. Cytokinins are a group of chemicals that primarily influence cell division and shoot formation but also have roles in delaying cell senescence, are responsible for mediating auxin transport throughout the plant, and affect internodal length and leaf growth. Auxins are compounds that positively influence cell enlargement, bud formation and root initiation. They also promote the production of other hormones and in conjunction with cytokinins, they control the growth of stems, roots, fruits and are involved in flowering.

In the method for producing sterile flowering biomass according to the invention, a natural or artificial cytokinin belonging to the adenine-type or the phenylurea-type is preferably used, more preferably said cytokinin is selected from adenine, kinetin, zeatin, 6-benzylaminopurine, diphenylurea (DPU), N-(2-chloro-4-pyridyl)-N-phenylurea (CPPU), thidiazuron (TDZ) and derivatives thereof having cytokinin activity, more preferably said cytokinin is selected from thidiazuron (TDZ), Benzylaminopurine (BAP), Meta-Topolin (mT), Kinetin (Kin), DPU or CPPU, most preferably from thidiazuron (TDZ), Benzylaminopurine (BAP), Meta-Topolin (mT), or Kinetin (Kin).

Based on common general knowledge, a skilled person will know which cytokinin(s) to select, depending on the type (plant species) and origin (explant type and part of plant from which it is directly or indirectly derived) of inoculated plant material.

In the case of a plant material from the family of Cannabaceae (preferably from *Cannabis* genera, in particular from *Cannabis sativa, Cannabis indica, Cannabis rudealis*, and hybrids thereof, most preferably from *Cannabis sativa* cultivars), preferred cytokinins comprised in the sterile culture medium in step a) are selected from thidiazuron (TDZ), Benzylaminopurine (BAP), Meta-Topolin (mT), or Kinetin (Kin), in particular said cytokinin(s) is/are thidiazuron (TDZ) and/or Meta-Topolin (mT).

With respect to cytokinin concentration, the sterile liquid culture medium in the temporary liquid immersion culture system preferably comprises from 0.01 to 10 mg/L, preferably from 0.1 to 5 mg/L of said cytokinin.

In the method for producing sterile flowering biomass according to the invention, the sterile liquid culture medium preferably further comprises another plant hormone, preferably an auxin, as defined above. Appropriate auxins for use in the invention include naturally occurring auxins, such as 4-chloro-indoleacetic acid, phenylacetic acid (PAA), indole-3-butyric acid (IBA) and indole-3-acetic acid (IAA); or synthetic auxin analogues, such as 1-naphthaleneacetic acid (NAA), and 2,4-dichlorophenoxyacetic acid (2,4-D).

When present, the concentration of auxin in the sterile liquid culture medium is from 0.01 to 10 mg/L, more preferably between 0.1 and 5 mg/L.

Inoculation

Inoculation is made by the more appropriate method, depending on the type of temporary liquid immersion culture system used.

Inoculum size typically ranges from 1 to 50 explants, preferably 1 to 10 explants or even 1 to 5 explants (in particular explants from nodal segments), per 100 ml of sterile culture medium. Usually, 3 explants are used to inoculate 100 ml medium (Watt, 2012).

Step b) (Growing Leafy Biomass)

"Leafy biomass" is an expression widely used in the domain of plant growing, and refers to plant material composed mainly of leaf tissue and stems, without excluding the occasional minor presence of other organs such as roots or flowers. Leaf tissue is distinguished from other plant tissues by their shape, their higher number of chloroplasts and developing chloroplasts (as counted by confocal microscopy analysis), and the higher photosynthetic activity (determination of Fv/Fm with fluorometer) and chlorophyll content (by analysis of extracted pigments by absorption spectrophotometry) of chloroplasts, as detected by the absorption of carbon dioxide by the plant tissue. Such methods of determination are well known to the skilled person as for example as described in (Baker (2008) Ann. Rev. Plant Biol. 59: 89-113). When referring to leafy biomass, it is intended to refer to plant material comprising at least 50%, preferably 70%, and more preferably greater than 85% leaf tissue.

"Growing leafy biomass" is thus intended to mean the growing of the biomass of inoculated plant material while maintaining at least 50%, preferably 70%, and more preferably greater than 85% of leaf tissue.

Sterile Liquid Culture Medium

The sterile liquid culture medium used in step b) for growing leafy biomass may or not have the same composition as the sterile liquid culture medium used in step a).

Preferably, the same basal culture medium as in step a) is used in step b), in order not to have to remove the culture medium from the temporary liquid immersion culture system.

The sterile liquid culture medium used in step b) also comprises at least one cytokinin and optionally at least one auxin, as defined above for the culture medium of step a).

However, various compounds may further be added in the sterile liquid culture medium of step b).

For instance, additional amounts of a sterile carbon source (preferably sucrose) may be added during step b), in order to ensure that sufficient carbon and energy supply is present in the culture medium during the whole duration of step b). When performed, addition of additional amounts of a sterile carbon source (preferably a sucrose solution) during step b) is performed under sterile conditions to ensure that the produced flowering biomass remains sterile.

Phytohormones (such as cytokinins, auxins or other phytohormones, more preferably cytokinins, where said cytokinins are selected from adenine, kinetin, zeatin, 6-benzylaminopurine, diphenylurea, thidiazuron (TDZ) and derivatives thereof having cytokinin activity) may also be added during step b) to compensate hormone degradation over time or to further optimize growth by inducing physiological changes in the plant material, notably affecting the development of axillary buds, development of leaves, and/or elongation of stems.

Duration and Frequency of Immersion

The "duration of immersion" is defined as the duration during which the plant material is immersed in the culture medium.

The "frequency of immersion" is defined as follows:

Frequency of immersion=1/duration in hours between two immersions of the plant material in the culture medium.

The frequency of immersion decreases when the duration between two immersions of the plant material in the culture medium increases. However, for practical reasons, in the following the frequency of immersion will in fact be expressed as a duration (in minutes or hours) between the starting time of two consecutive immersions of the plant material in the culture medium.

In step b) of growing leafy biomass, the duration and frequency of immersion of the plant material in the culture medium preferably varies from 30 seconds to 15 minutes every 30 minutes to 12 hours.

Depending on the type (plant species) and origin (explant type and part of plant from which it is directly or indirectly derived) of plant material inoculated in step a), a skilled person will be able to optimize the duration and frequency of immersion of the plant material in the culture medium in step b) in order to favor the growing leafy biomass.

For most plants, in step b), a duration and frequency of immersion of the plant material in the culture medium from 1 to 10 minutes every 2 to 8 hours, more preferably from 1 to 5 minutes every 4 to 8 hours will be appropriate.

For most plants, and particularly in the case of a plant material from the family of Cannabaceae (preferably from *Cannabis* genera, in particular from *Cannabis sativa*, *Cannabis indica*, *Cannabis rudealis*, and hybrids thereof, most preferably from *Cannabis sativa* cultivars), a duration and frequency of immersion of the plant material in the culture medium from 2 to 4 minutes every 4 to 8 hours, more preferably from 2.5 to 3.5 minutes every 5 to 7 hours, most preferably 3 minutes every 6 hours will be used in step b).

However, other appropriate durations and frequencies may be determined by a skilled person based on common general knowledge about the plant material of interest. The goal of the duration and frequency of immersion is to ensure the plant material maintains a degree of humidity that is favorable for growing leafy biomass.

Therefore, while the above-mentioned durations and frequencies are examples of appropriate durations and frequencies, alternative appropriate (duration/frequency) combinations, in which duration is decreased and frequency increased or duration is increased and frequency is decreased, may be determined by a skilled artisan.

In particular, for optimization of the duration and frequency of immersion in step b) of growing leafy biomass, various durations and frequencies may be tested and the weight total leafy biomass produced (i.e. the total yield) and plant material quality monitored to identify the best immersion conditions.

Light Conditions

Depending on the type (plant species) and origin (explant type and part of plant from which it is directly or indirectly derived) of plant material inoculated in step a), a skilled person will know which appropriate light conditions for growing leafy biomass should be used in step b), based on common general knowledge about the plant material of interest.

Relevant light parameters that may be optimized include:
photoperiod,
light type (wavelength notably), and
light intensity.

Photoperiod refers to the time that a plant or animal is exposed to light over a given period of time, usually over 24-hour. In step b), an appropriate photoperiod may be a regimen of 12 to 18 hours of light and 6 to 12 hours of darkness, preferably 14 to 18 hours of light and 6 to 10 hours of darkness, such as 16 hours of light and 8 hours of darkness or 12 hours of light and 12 hours of darkness.

Light can be supplied as white light which includes the entire spectrum, as red (~625-700 nm) and blue (~450-520 nm) lights (corresponding to the absorption peaks of chlorophyll), or as a mix thereof. Other wavelengths might be involved in growth and tissue differentiation, such as flowering or flower maturation, and might thus be added.

Light intensity is preferably in ranges from 50-600 µmol photons/m2/s of Photosynthetically Active Radiations (PAR), preferably 100-300 µmol photons/$m^2$/s.

Other Culture Parameters

Depending on the type (plant species) and origin (explant type and part of plant from which it is directly or indirectly derived) of plant material inoculated in step a), further culture parameters may be optimized by a skilled person for growing leafy biomass, based on common general knowledge about the plant material of interest.

These may notably include:

Temperature:

Temperature is a species-dependent parameter and may be optimized for cultures between 5 to 35° C., preferably between 10 to 35° C., and more specifically between 18 and 35° C. (more preferably about 27° C.) in the case of a plant material from the family of Cannabaceae (preferably from *Cannabis* genera, in particular from *Cannabis sativa*, *Cannabis indica*, *Cannabis rudealis*, and hybrids thereof, most preferably from *Cannabis sativa* cultivars) (Potter, 2014).

Gas composition:

Gas composition is to be controlled and can be optimized for growth and production by enriching the air in either CO2 or O2. The use of air enriched with 40% O2 is particularly promising (Florez et al., 2016).

In the case of a plant material from the family of Cannabaceae (preferably from *Cannabis* genera, in particular from *Cannabis sativa, Cannabis indica, Cannabis rudealis*, and hybrids thereof, most preferably from *Cannabis sativa* cultivars), a temperature between 18 and 35° C. (more preferably about 27° C.), a CO2 concentration of 0.05 to 5%, and an O2 concentration of 5 to 50% will preferably use used in step b).

Step c) (Inducing and Maturing Flower Tissues from the Leafy Biomass)

Sterile Liquid Culture Medium

The sterile liquid culture medium used in step c) for inducing and maturing flower tissues from the leafy biomass may or not have the same composition as the sterile liquid culture medium used in step b).

Preferably, the same basal culture medium as in steps a) and b) is used in step c), in order not to have to remove the culture medium from the temporary liquid immersion culture system.

The sterile liquid culture medium used in step c) also comprises at least one cytokinin and optionally at least one auxin, as defined above for the culture medium of steps a) and b).

However, various compounds may further be added in the sterile liquid culture medium of step b).

For instance, additional amounts of a sterile carbon source (preferably sucrose) may be added at the beginning and/or during step c), in order to ensure that sufficient carbon and energy supply is present in the culture medium during the whole duration of step c). When performed, addition of supplemental amounts of a sterile carbon source (preferably a sucrose solution) during step c) is performed under sterile conditions to ensure that the produced flowering biomass remains sterile. Moreover, when the interest of the flowering biomass resides in one or more compound(s) naturally produced in flowers, elicitors able to enhance the production of the compound(s) of interest may be added under sterile conditions at the start or during step c).

In the case of a plant material from the family of Cannabaceae (preferably from *Cannabis* genera, in particular from *Cannabis sativa, Cannabis indica, Cannabis rudealis*, and crossings cultivars thereof, most preferably from *Cannabis sativa* cultivars), an elicitor selected from biotic or abiotic elicitors may notably be added under sterile conditions in step c) (usually during or at the end of step c)).

For instance, biotic elicitors include but are not limited to insect, bacterial and fungal extracts. Abiotic elicitors include but are not limited to chemical treatments such as phytohormones, plants secondary messengers, osmotic agents, surfactants, high affinity resins, environmental parameters (including notably temperature or light changes on a short duration), metal salts, oxidants or combinations thereof.

Preferably, elicitors are added 1-10 days before harvest.

Duration and Frequency of Immersion

In the method for producing sterile flowering biomass according to the invention, flowering is induced by reducing the duration and/or frequency of the immersion of the plant material in the culture medium in step c) compared to step b).

The duration and frequency of immersion of the plant material in the culture medium in step c) also varies from 30 seconds to 15 minutes every 30 minutes to 12 hours, preferably from 1 to 10 minutes every 2 to 8 hours, more preferably from 1 to 5 minutes every 4 to 8 hours.

The percentage of reduction of the duration and/or frequency of immersion of the plant material in the culture medium between step c) and step b) is calculated based on the total daily immersion duration, as follows:

Percentage of reduction of the duration and/or frequency of immersion of the plant material in the culture medium between step c) and step b)=Total daily immersion during step c)/Total daily immersion during step b)×100, wherein the total daily immersion of step b) or c) is calculated as follows:

Total daily immersion=immersion duration×24×frequency of immersion=immersion duration×24/duration in hours between two immersions of the plant material in the culture medium.

However, the duration and/or frequency of immersion of the plant material in the culture medium in step c) is reduced by 15 to 70%, preferably by 20 to 60%, more preferably by 25 to 50%, most preferably by 30 to 40% or by 30 to 35% in step c) compared to step b).

In a preferred embodiment of the method for producing sterile flowering biomass according to the invention, only the duration of immersion of the plant material in the culture medium is reduced in step c) compared to step b), by about 30 to 40%.

More preferably:
  the plant material is immersed in the culture medium every 4 to 8 hours, more preferably every 5 to 7 hours, most preferably every 6 hours,
  the duration of immersion of the plant material in the culture medium in step b) is from 2 to 4 minutes, more preferably from 2.5 to 3.5 minutes, most preferably 3 minutes,
  the duration of immersion of the plant material in the culture medium in step c) is from 1 to 3 minutes, more preferably from 1.5 to 2.5 minutes, most preferably 2 minutes, and
  the duration of immersion of the plant material in the culture medium in step c) is 1 to 2 minutes shorter than in step b).

Light Conditions

Light conditions (photoperiod, light type and light intensity) used in step c) may be the same as in step b). Therefore, in a preferred embodiment, light conditions (photoperiod, light type and light intensity) used in step c) are the same as in step b).

However, light conditions may also be changed between steps b) and c), and/or during step c), in order to improve flowering or accumulation of products of interest in the flowers.

Therefore, in an embodiment, light conditions are also changed between steps b) and c), preferably by:
  reducing photoperiod in step c) compared to step b), more preferably from a regimen of 16 hours of light and 8 hours of darkness to a regimen of 12 hours of light and 12 hours of darkness, or 8 hours of light and 16 hours of darkness; and/or
  changing the type of light by providing a higher proportion of red radiations (~625-700 nm) in step c) compared to step b), more preferably by adding 50-200 µmol photons/m$^2$/s red radiations in step c) to the light used in step b); and/or
  increasing light intensity.

For instance, while light intensity in step b) is preferably from 50-600 µmol photons/m$^2$/s, more preferably 100-300 µmol photons/m$^2$/s, light intensity in step c) may be raised to a higher light intensity, between 100-900 µmol photons/m$^2$/s, more preferably to 200-500 µmol/m$^2$/s.

The increase in light intensity in step b) compared to step c) is preferably of 30-100%.

Preferred Embodiments of the Method for Producing Sterile Flowering Biomass

In a preferred embodiment of the method for producing sterile flowering biomass according to the invention:
- the sterile plant material is selected from the family of Cannabaceae will preferably be used, more preferably from *Cannabis* genera, in particular from *Cannabis sativa, Cannabis indica, Cannabis rudealis*, and hybrids thereof,
- the temporary liquid immersion culture system is a temporary immersion bioreactors (TIB) containing a volume of sterile liquid culture medium comprised from 1 to 1000 L, from 1 to 500 L, more preferably from 1 to 300 L, from 1 to 100 L, from 1 to 50 L, or from 1 to 10 L, depending on the desired scale-up for the production,
- at least one cytokinin present in the sterile liquid culture medium of steps a) to c) is selected from thidiazuron (TDZ), Benzylaminopurine (BAP), Meta-Topolin (mT), or Kinetin (Kin), preferably at least one cytokinin is thidiazuron (TDZ) or Meta-Topolin (mT), and is present in a concentration from 0.1 to 10 mg/L in said culture medium, and
- the durations and frequencies of immersion of the plant material in the culture medium in steps b) and c) are from 1 to 10 minutes every 2 to 8 hours, and the duration and/or frequency of immersion is reduced by 25 to 50%, preferably by 30 to 40% in step c) compared to step b).

In this preferred embodiment, the method may further include one or more of the following features:
i) a light photoperiod comprised between 8 to 16 hours of light and 8 to 16 hours of darkness, the photoperiod being optionally decreased in step c) compared to step b).
ii) a temperature between 18 and 35° C. in steps b) and c), and more preferably about 27° C.,
iii) a gas composition made of air enriched with 20% to 60% O2 (preferably 30% to 50%, and more preferably about 40% O2),
iv) a sterile liquid culture medium derived from MS or B5 medium, supplemented with 2 to 4% sucrose (i.e 0.20 to 40 g/L), more preferably about 3% (i.e. 30 g/L) sucrose.

In a particularly preferred embodiment of the method for producing sterile flowering biomass according to the invention:
- the sterile plant material is selected from *Cannabis sativa* cultivars,
- the temporary liquid immersion culture system is a temporary immersion bioreactors (TIB) containing a volume of sterile liquid culture medium from 1 to 300 L,
- the cytokinin present in the culture medium of steps a) to c) is selected from thidiazuron (TDZ), Benzylaminopurine (BAP), Meta-Topolin (mT), or Kinetin (Kin), preferably the cytokinin is thidiazuron (TDZ) or Meta-Topolin (mT), and is present in a concentration from 0.1 to 10 mg/L in said culture medium, and
- the duration and frequencies of immersion of the plant material in the culture medium in steps b) and c) are the following:
  step b):
    duration: 2 to 4 minutes, preferably from 2.5 to 3.5 minutes, more preferably 3 minutes
    frequency: once every 4 to 8 hours, preferably once every 5 to 7 hours, more preferably once every 6 hours,
  step c):
    duration: 1 to 3 minutes, preferably from 1.5 to 2.5 minutes, more preferably 2 minutes, wherein the duration of immersion of the plant material in the culture medium in step c) is 1 to 2 minutes shorter than in step b),
    frequency: once every 4 to 8 hours, preferably once every 5 to 7 hours, more preferably once every 6 hours.

In this preferred embodiment, the method may further include one or more of the following features:
i) a light photoperiod comprised between 8 to 16 hours of light and 8 to 16 hours of darkness, the photoperiod being optionally decreased in step c) compared to step b).
ii) a temperature between 18 and 35° C. in steps b) and c), and more preferably about 27° C.,
iii) a gas composition made of air enriched with 20% to 60% O2 (preferably 30% to 50%, and more preferably about 40% O2),
iv) a sterile liquid culture medium derived from MS or B5 medium, supplemented with 2 to 4% sucrose, more preferably about 3%.

Method for Producing a Component Present in Flowering Biomass

The present invention also relates to a method for producing at least one component present in flowering biomass, the method comprising:
a) producing sterile flowering biomass from sterile plant material using the method according to the invention as disclosed herein, and
b) collecting or extracting the component(s) from the obtained sterile flowering biomass or culture medium.

The method may further comprise:
c) purifying the collected or extracted component(s), and
d) optionally, adding an acceptable diluent, excipient or carrier to the purified component(s).

Collection or Extraction of Components

The collection or extraction of the component(s) of interest will be done according to standard methods known in the art.

When the component(s) of interest is(are) easily released or secreted outside of the flower tissue (such as safranal and picrocrocins in *Crocus sativus*), and is(are) water soluble, it(they) may be directly extracted from the culture medium, without a need for extraction from plant tissues.

For component(s) of interest that are produced inside the flower tissue, the component(s) of interest is (are) extracted from the flowering tissue or both the flowering and leafy tissues according to standard methods known in the art.

These methods include but are not limited to drying the flowering tissue or both the flowering and leafy tissues and crushing it, before extracting the component(s) of interest from the plant tissue powder. Extraction is usually performed by supercritical CO2 extraction, solvent extraction such as ethanol, glycerin or water. In a preferred embodiment, Cannabinoids are extracted using ethanol or supercritical $CO_2$ extraction.

Purification of Collected or Extracted Component

Further to its (their) collection or extraction, the component(s) of interest may optionally be further purified, depending on its (their) intended use.

For non-pharmaceutical uses, plant extracts may usually be used without further purification. However, for pharmaceutical uses, substantially purified compounds (substantially pure form typically contains at least 90%, or at least 95% or at least 99% of the component) are preferred, and the method for producing a component present in flowering biomass according to the invention may then comprise one or more purification steps.

Depending on the component(s) of interest, a skilled person will be able to design appropriate purification steps, based on common general knowledge in this respect.

For instance, when component(s) of interest comprise one or more cannabinoid compounds (see below for more details), suitable purification steps may include preparatory chromatography using normal phase or reverse phase columns, allowing the separation of the extract in different fractions. Fractions may be further purified by similar methods or by evaporation and resuspension of the compounds in a specific solvent, in which impurities are insoluble. In a preferred embodiment, cannabinoids extracted with supercritical CO2 are first winterized: the extract is dissolved in ethanol, stored at −20° C. until solidification of the co-extracted oil and waxes, and filtered to remove the oil and waxes. The extract is then further purified in the same manner as an extract obtained from ethanol extraction on plant tissue powder, preferably by using C18 reverse phase columns.

Addition of Acceptable Diluent, Excipient or Carrier

Depending on its (their) intended use, an acceptable diluent, excipient or carrier may be added to the (optionally purified) component(s) of interest.

Diluents, excipients, or carriers include, but are not limited to oils (notably pure, as micelles, or as microdroplets), cyclodextrins, or solvents such as ethanol, glycerin, and water.

Main Components of Interest

While the method for producing at least one component present in flowering biomass according to the invention may be performed for producing any type of component present in flowering biomass, some specific components are preferred. These include cannabinoids, morphine, helenaline, safranal and picrocrocin.

Cannabinoids are accumulated in glandular trichomes that occur most abundantly on the floral calyxes and bracts of female plants of the genus *Cannabis*. As a drug it usually comes in the form of dried flower buds (marijuana), resin (hashish), or various extracts collectively known as *cannabis* oil.

More than 130 distinct cannabinoid compounds have been described as present in plants of the genus *Cannabis* (Berman et al., 2018). Most cannabinoids exist in two forms, as acids and in neutral (decarboxylated) forms. The acid form is the one usually found in nature, designated by an "A" at the end of its acronym (i.e. THCA is the acidic form of THC), whereas the decarboxylated form is usually formed by heating. The two cannabinoids usually produced in greatest abundance are cannabidiolic acid (CBDA) and/or tetrahydrocannabinolic acid (THCA). THC is psychoactive while CBD, CBDA and THCA are not.

In a preferred embodiment of the method for producing at least one component present in flowering biomass according to the invention, the plant is selected from the genus *Cannabis* (preferably from *Cannabis sativa*, *Cannabis indica*, *Cannabis rudealis*, and hybrids thereof, more preferably *Cannabis sativa* cultivars), and said component is at least one cannabinoid compound, preferably said cannabinoid compound is one or more of tetrahydrocannabinol (THC), tetrahydrocannabinolic acid (THCA), cannabigerol (CBG), cannabigerolic acid (CBGA), cannabidiol (CBD), cannabidiolic acid (CBDA), cannabichromene (CBC), and cannabichromenolic acid (CBCA).

The following examples intend to illustrate the present invention.

EXAMPLES

The research program presented in the present Examples has been authorized by the French drug administration (Agence nationale de sécurité du medicament et des produits de santé "ANSM"), under authorization number A-2018-10-893-S.

Example 1: Significant Effect of Reducing Duration of Immersion on *Cannabis sativa* Cultivars' Flowering in TIB The effect of the duration of immersion on *Cannabis sativa* cultivars' flowering in TIB was then tested.

Materials and Methods

*Cannabis* Cultivars

All *cannabis* cultivars have been obtained from the University of Leyden in Netherlands.

Five different *Cannabis* cultivars (strains A to E; with A=Caramel, B=Purple Haze, C=Amazing Haze, D=Blue Amnesia, and E=Cannatonic) were selected to represent a range of chemotypes, sizes, photoperiod responses and genetic backgrounds.

In Vitro TIB Culture of *Cannabis* Cultivars

In vitro cultures were established from surface-sterilized seeds germinated on MS medium supplemented with 3% sucrose. Nodal explants from plantlets were subcultured and multiplied on MS medium supplemented with 0.5 mg/L TDZ or 0.5 mg/L mT. RITA® bioreactors were inoculated with 1-5 g nodal explants and cultivated for 4 weeks under 16 h light/8 h night photoperiod and 3 min immersions every 6 h. After this first biomass proliferation step, immersion frequency was set at 2 min every 6 h to induce flowering. Flowering was monitored over 3-6 following weeks.

Determination of Dry Weight Percentage

Samples were weighted before (Fresh weight, FW) and after (Dry Weight, DW) freeze-drying. Dry biomass was then ground with a mortar and pestle before extraction for cannabinoid content analysis.

Analysis of Cannabinoid Content

Extraction of cannabinoids: 30 mg DW were extracted three times with 1 ml Ethanol 96% (HPLC grade), filtered on 0.2 μm nylon filters in 2 ml glass vials and analyzed by HPLC.

HPLC analysis: HPLC analysis were conducted on a Chromaster (Hitachi) 600 bars system, with a gradient pump 5160, sampler 5260, column oven 5310, pump with degasser 5160, diode array detector DAD 5430, Chromaster software, connected to a Dell Optiplex 3040 PC. Separation was done using a Kinetex® Core Shell C18 column (Phenomenex, 2.6 μm, 100A, 150×3 mm), protected by a precolumn (Phenomenex, SecurityGuard™ ULTRA Cartridges, UHPLC C18 3.0 mm ID Columns, mounted on SecurityGuard™ ULTRA Holder for UHPLC Columns 2.1 to 4.6 mm ID). The mobile phase is composed of A: water+0.1% Formic Acid (AF), B: Methanol+0.1% AF. Flow is set to 0.7 ml/min, and oven temperature at 50° C. 10 μl sample are injected. The separation gradient starts from 70% B, up to 85% B in 20 min, followed by 95% B for 5 min and back to 70% for 5 min. Detection is done at 230 nm. Quantification of main cannabinoids is done using 11 analytical standards (Merck-Sigma Aldrich): CBDV, THCV, CBD, CBG, CBDA, CBGA, CBN, THC, CBC, THCA, and CBCA.

Results

In Vitro Flowering of 5 Different *Cannabis sativa* Cultivars

Figure 1:
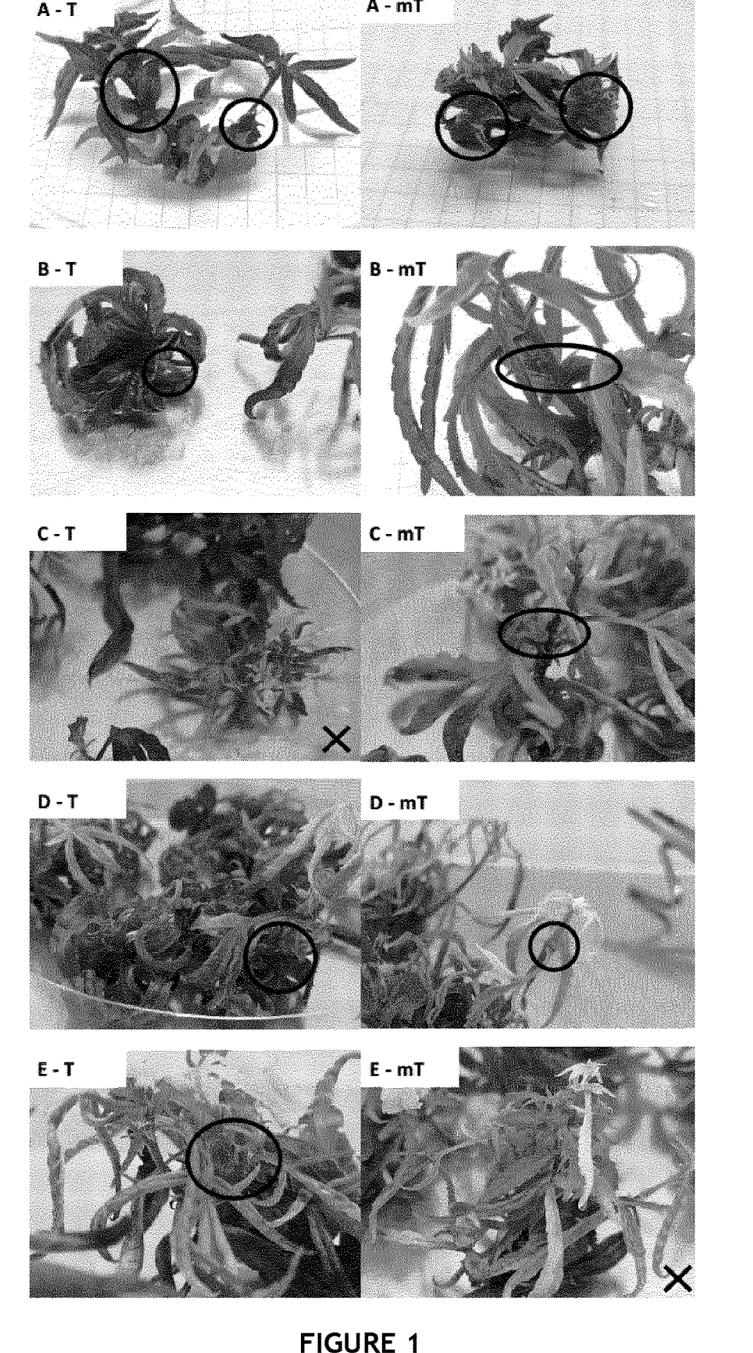
FIG. 1. *Cannabis* flowers observed on strains A to E (with A=Caramel, B=Purple Haze, C=Amazing Haze, D=Blue Amnesia, and E=Cannatonic). T: culture media with TDZ, mT: culture media with meta-topolin. Strain C grown on T and strain E and grown on mT did not show any flowers in the duration on the experiment. D—mT shows a male *cannabis* flower. Other conditions all showed female *cannabis* flowers, which are shown by a circle around each flower.

The above-described in vitro culture of *Cannabis sativa* cultivars in RITA TIB resulted in flowering after only 3-6 weeks after reducing the immersion to 2 minutes every 6 hours (see FIG. 1).

Although testing only 2 distinct cytokinins, and without optimizing other parameters, a significant number of flowers were obtained for all 5 (4 female and 1 male) tested *Cannabis sativa* cultivars. In 2 cases, one of the cultivars showed flowers with one of the two tested cytokinins. Flowering with the other tested cytokinin in those two cases is expected to occur within the weeks after the chosen observation time. This suggests that the cytokinin can influence flowering time for some cultivars. Example 2 shows the flowering of Cannatonic (FIG. 1E) using another cytokinin after an extra 4 weeks cultivation, supporting this point and confirming the suitability of the tested method to produce sterile flowering biomass in temporary immersion bioreactors for various *Cannabis sativa* cultivars.

Dry Weight Percentage and Cannabinoid Production

In *cannabis*, the density of glandular trichomes is clearly superior on floral tissues compared to leafy biomass. As glandular trichomes are a preferential cannabinoid accumulation site, cannabinoid contents were measured in those tissues and compared to the cannabinoid content of the rest of the biomass.

The ratio DW/FW was around 15-20% for all samples (data not shown). Floral biomass represents up to 66% of total fresh weight.

Figure 2:
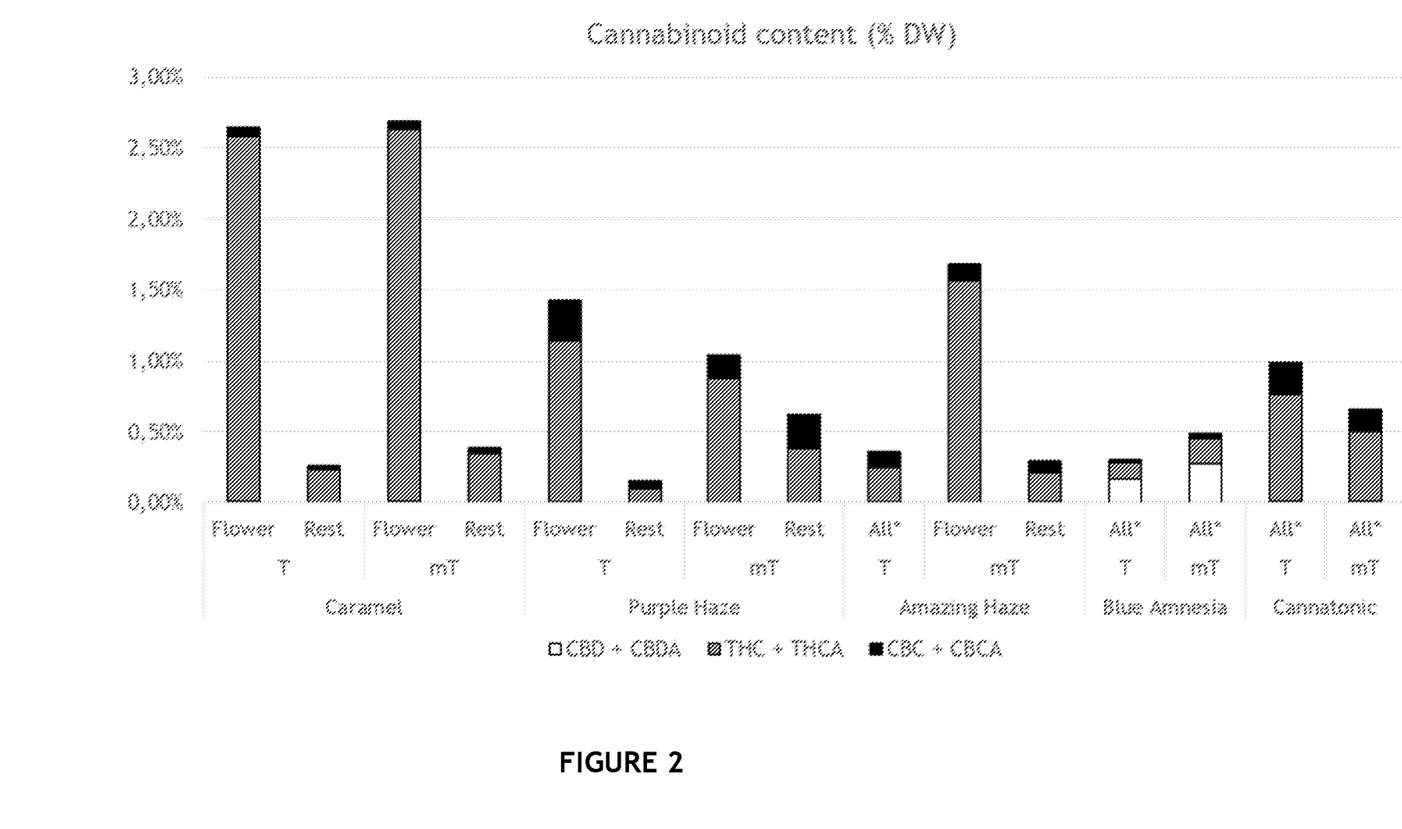

Results of cannabinoid content analysis are presented in FIG. 2, and shows that a significant increase in cannabinoid content, reaching up to 10-fold, is observed in female flowers in comparison to the rest of the biomass. Male flowers represented too little biomass to allow extraction and were not expected to change in terms of cannabinoid content, they were thus not tested.

The main cannabinoid detected was THC and its decarboxylated form THCA for all tested strains except strain D, which seemed to be the only one to produce significant amounts of CBD+CBDA in those conditions. CBCA and its decarboxylated form CBC were also detected in lower content in all 5 tested strains in the tested conditions.

CONCLUSIONS

The above results show that duration of immersion is an essential parameter for flowering of *cannabis* strains in TIB. Reducing the duration of immersion compared to the usual duration used for growing leafy biomass resulted in rapid (3-6 weeks) flowering of all tested *cannabis* strains.

It should be stressed that these positive results have been obtained using conventional culture medium composition and light parameters, suggesting that flowering may be further improved, for each *cannabis* strain of interest, by optimizing other culture parameters.

With respect to cannabinoid production, the above results also show that flowering results in significant increase of total cannabinoid content, most of the cannabinoid content being found in female flowers.

Concerning contents, while the total content may somewhat vary depending on the precise *Cannabis sativa* cultivars and the specific cytokinin used in culture medium, a content of at least about 1% of dry weight has been obtained for 4 out of the 5 tested cultivars, and a content of at least about 1.5% of dry weight has been obtained for 3 out of the 5 tested cultivars. Here also, it should be stressed that these positive results have been obtained using conventional culture medium composition and light parameters. In particular no elicitor intended to improve cannabinoids accumulation in the flowers has been used, suggesting that contents in cannabinoids may further be improved.

With respect to the type of cannabinoids produced, mainly THC+THCA was produced, as well as a low level of CBC+CBCA. However, it may be expected that addition of various elicitors to the culture medium could potentially alter the quantity of cannabinoids produced, their relative abundance and stimulate the production of rare cannabinoids.

Example 2: Photoperiod is not Crucial for *Cannabis sativa* Flowering in TIB

Two photoperiod conditions were tested on *Cannabis sativa*, strain Cannatonic to evaluate its effect on flowering for TIB grown material.

Materials and Methods

*Cannabis* Cultivar

The same *Cannabis sativa* cultivar Cannatonic tested in Example 1 was used to evaluate the effect of this parameter on flowering.

Culture Conditions and Change of Photoperiod

Two RITA® bioreactors were inoculated with approximately 1 g nodal explants and cultivated for 4 weeks under 16 h light/8 h dark, in liquid MS medium, supplemented with 3% sucrose and 0.5 mg/L BAP. Immersion time was set to 2 min immersion every 6 h. After 4 weeks cultivation, the culture medium was renewed, one bioreactor was kept under long day (16 h day/8 h night) and the other was transferred to short day (12 h day/12 h night). Plants were observed 4 weeks after change of photoperiod.

Results

In Vitro Flowering Under the Two Photoperiod Conditions

Figure 3:
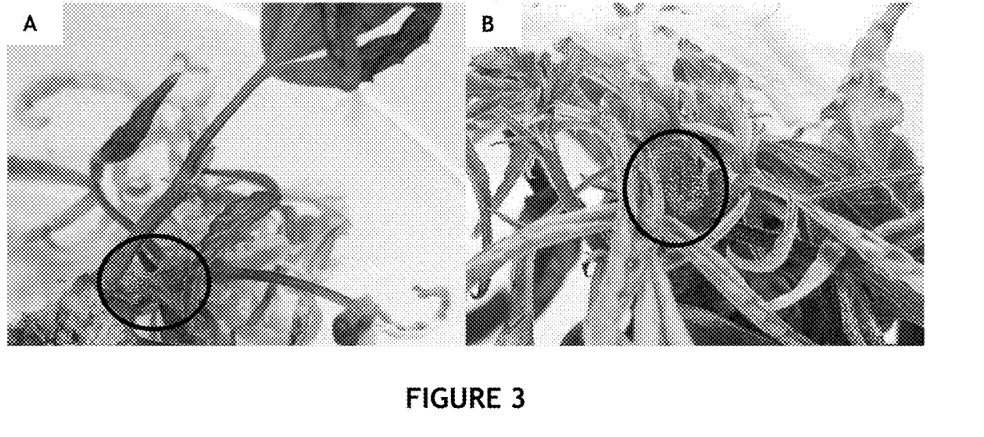
FIG. 3. Flowering of *Cannabis sativa* cultivar Cannatonic grown under (A): 16 h/8 h, or (B): 12 h/12 h photoperiod. Female flowers are circled in black.

Female flowers were observed for the bioreactor grown under 16 h/8 h photoperiod (FIG. 3A). Similar flowers in terms of size and development were observed in bioreactor grown under 12 h/12 h (FIG. 3B).

CONCLUSIONS

Photoperiod is known to be a very important parameter for the induction of flowering in many plant species. Notably, *Cannabis sativa*'s flowering is commonly induced ex-vitro by shortening of the photoperiod from 16 h light/8 h dark to 12 h light/12 h dark. In "autoflowering" cultivars, ex-vitro flowering occurs naturally after a given culture time.

Although further tests would be needed to confirm those results in broader conditions, the above results show that the change of photoperiod is not necessary for the induction of flowering in TIB. Moreover, no significant effect on the time or density of development of flowers were observed in the tested conditions, suggesting that flower development was comparable in those conditions.

In the tested conditions, the photoperiod has thus had no visible effect on induction of flowering nor flower development, provided that immersion time is reduced after growing leafy biomass.

BIBLIOGRAPHIC REFERENCES

1. Alvard D., Cote, F., and Teisson, C. (1993). Comparison of methods of liquid medium culture for banana micropropagation: effects of temporary immersion of explants. Plant Cell, Tissue and Organ Culture, 32, 55-60.

2. Baker (2008) Ann. Rev. Plant Biol. 59: 89-113.
3. Berman P., Futoran K., Lewitus G. M., Mukha D., Benami M., Shlomi T., Meiri D. (2018). A new ESI-LC/MS approach for comprehensive metabolic profiling of phytocannabinoids in *Cannabis*. Sci Rep. 8(1), 14280.
4. Chandra, S., Lata, H., ElSohly, M. A., Walker, L. A., and Potter, D. (2017). *Cannabis* cultivation: Methodological issues for obtaining medical-grade product. Epilepsy Behav. 70, 302-312.
5. Driver and Kuniyaki Walnut medium, Driver J A, Kuniyuki A H, 1984, In vitro propagation of Paradox walnut rootstock. Hortscience 19: 507-509.
6. Etienne, H., and Berthouly, M. (2002). Temporary immersion systems in plant micropropagation. Plant Cell Tissue Organ Cult. 69, 215-231.
7. Florez, S. L., Curtis, M. S., Shaw, S. E., Hamaker, N. K., Larsen, J. S., and Curtis, W. R. (2016). A temporary immersion plant propagation bioreactor with decoupled gas and liquid flows for enhanced control of gas phase. Biotechnol. Prog. 32, 337-345.
8. Georgiev, V., Schumann, A., Pavlov, A., and Bley, T. (2014). Temporary immersion systems in plant biotechnology. Eng. Life Sci. 14, 607-621.
9. Lata, H., Chandra, S., Khan, I., and ElSohly, M. A. (2009). Thidiazuron-induced high-frequency direct shoot organogenesis of *Cannabis sativa* L. Vitro Cell. Dev. Biol.—Plant 45, 12-19.
10. Lata, H., Chandra, S., Khan, I. A., and ElSohly, M. A. (2010). High Frequency Plant Regeneration from Leaf Derived Callus of High Δ9-Tetrahydrocannabinol Yielding *Cannabis sativa* L. Planta Med. 76, 1629-1633.
11. Lata, H., Chandra, S., Khan, I. A., and ElSohly, M. A. (2016). In Vitro Propagation of *Cannabis sativa* L. and Evaluation of Regenerated Plants for Genetic Fidelity and Cannabinoids Content for Quality Assurance. In Protocols for In Vitro Cultures and Secondary Metabolite Analysis of Aromatic and Medicinal Plants, 2, 275-288.
12. Potter, D. J. (2014). A review of the cultivation and processing of *cannabis* (*Cannabis sativa* L.) for production of prescription medicines in the UK. Drug Test. Anal. 6, 31-38.
13. Romocea, J., and Grassi, G. (2010). "In vitro" propagation of *Cannabis sativa* I. Var. Ermo., Conference paper.
14. Sri et al. "In vitro flowering—A review", Journal of Agricultural Technology, 1 Oct. 2012 (2012-10-01), pages 1517-1536.
15. Wang, R, Li-Si, H., Xia, B., Jin-Feng, T., Li, N. and T., and Peng, F., et al. (2009). A micropropagation system for cloning of Hemp (*Cannabis sativa* L.) shoot tip culture. Pak. J. Bot., 41(2), 603-608.
16. Watt, M. P. (2012). The status of temporary immersion system (TIS) technology for plant micropropagation. Afr. J. Biotechnol. 11, 14025-14035.
17. WO2011030083. Michoux, F., Nixon, P., and Mccarthy, J. (2011). Procédé. Imperial Innovations Limited, England.
18. WO 2012146872 A1. Etienne H., Georget F. and Bertrand B. (2012). Récipient pour la culture in vitro de matériel végétal en conditions steriles, par immersion temporaire. Centre De Coopération Internationale En Recherche Agronomique Pour Le Developpement (CIRAD), France.
19. WO2016092098. Michoux, F., and Boehm, M. (2016). Bioréacteur, Evonik Advanced Botanicals SAS, France.
20. WO2019006466. Heinricher, J. (2019a). Compositions and Methods for Large-Scale in Vitro Plant Bioculture. BOOSHOOT LLC, USA.
21. WO2019006470. Heinricher, J. (2019b). Milieux Pour Une Culture Tissulaire Rapide Et Fiable De Plantes. BOOSHOOT LLC, USA.
22. WO96/25484. Teisson, C. (1997). In vitro culture container. Centre De Coopération Internationale En Recherche Agronomique Pour Le Developpement (CIRAD), France. French registration: FR2730743

The invention claimed is:

1. A method for producing sterile flowering biomass from plant material selected from the family of Cannabaceae, the method comprising:
   a) inoculating a temporary liquid immersion culture system containing a sterile culture medium containing at least one cytokinin with sterile plant material,
   b) growing leafy biomass, and
   c) inducing and maturing flower tissues from the leafy biomass, wherein flowering is induced by reducing the duration and/or frequency of the immersion of the plant material in the culture medium in step c) compared to step b).

2. The method according to claim 1, wherein said sterile plant material is selected from cells, stems, leaves, meristems, internodes, floral organs or roots grown in sterile conditions or regenerated in sterile conditions from callus from a plant selected from the *Cannabis* genera.

3. The method according to claim 2, wherein said sterile plant material is selected from cells, stems, leaves, meristems, internodes, floral organs or roots grown in sterile conditions or regenerated in sterile conditions from callus from *Cannabis sativa* cultivars.

4. The method according to claim 1, wherein said temporary liquid immersion culture system is a temporary immersion bioreactor (TIB).

5. The method according to claim 4, wherein the volume of sterile liquid culture medium in said TIB is from 1 to 10 000 L.

6. The method according to claim 1, wherein said cytokinin is a natural or artificial cytokinin belonging to the adenine-type or the phenylurea-type.

7. The method according to claim 1, wherein said sterile liquid culture medium comprises from 0.01 to 10 mg/L.

8. The method according to claim 1, wherein said sterile liquid culture medium further comprises another plant hormone.

9. The method according to claim 8, wherein said other plant hormone is an auxin.

10. The method according to claim 1, wherein the duration and frequency of immersion of the plant material in the culture medium in steps b) and c) varies from 30 seconds to 15 minutes every 30 minutes to 12 hours.

11. The method according to claim 1, wherein the duration and/or frequency of immersion of the plant material in the culture medium in step c) is reduced by 15 to 70% in step c) compared to step b).

12. The method according to claim 11, wherein the duration and/or frequency of immersion of the plant material in the culture medium in step c) is reduced by 30 to 40% in step c) compared to step b).

13. The method according to claim 11, wherein only the duration of immersion of the plant material in the culture medium is reduced in step c) compared to step b).

14. The method according to claim 13, wherein:
   the plant material is immersed in the culture medium with a frequency of once every 4 to 8 hours,
   the duration of immersion of the plant material in the culture medium in step b) is from 2 to 4 minutes, the duration of immersion of the plant material in the culture medium in step c) is from 1 to 3 minutes, and the duration of immersion of the plant material in the culture medium in step c) is 25% to 50% shorter than in step b).

15. The method according to claim 1, wherein light conditions are also changed between steps b) and c), by:

reducing photoperiod in step c) compared to step b); and/or changing the type of light by providing a higher proportion of red radiations (~625-700 nm) in step c) compared to step b); and/or increasing light intensity.

16. The method according to claim 1, wherein an elicitor selected from biotic or abiotic elicitors is added under sterile conditions in step c).

17. The method according to claim 1, wherein:

said sterile plant material is selected from *Cannabis sativa* cultivars, said temporary liquid immersion culture system is a temporary immersion bioreactor (TIB) containing a volume of sterile liquid culture medium from 1 to 300 L, said cytokinin is selected from thidiazuron (TDZ), Benzylaminopurine (BAP), Meta-Topolin (mT), or Kinetin (Kin), and is present in a concentration from 0.1 to 10 mg/L in said sterile liquid culture medium, and the duration and frequencies of immersion of the plant material in the culture medium in steps b) and c) are the following:

step b):
  duration: 2 to 4 minutes,
  frequency: once every 4 to 8 hours, step c):
  duration: 1 to 3 minutes, wherein the duration of immersion of the plant material in the culture medium in step c) is 25% to 50% shorter than in step b),
  frequency: once every 4 to 8 hours.

18. A method for producing a component present in flowering biomass, the method comprising:

a) producing sterile flowering biomass from sterile plant material using the method according to claim 16, and b) collecting or extracting the component from the obtained sterile flowering biomass.

19. The method according to claim 18, wherein said plant is selected from *Cannabis sativa* cultivars, and said component is at least one cannabinoid compound.

* * * * *